US008383579B2

(12) United States Patent
Kirsh et al.

(10) Patent No.: US 8,383,579 B2
(45) Date of Patent: *Feb. 26, 2013

(54) METHOD FOR CUSTOMIZED DISPENSING OF VARIABLE DOSE DRUG COMBINATION PRODUCTS FOR INDIVIDUALIZING OF THERAPIES

(75) Inventors: Richard L. Kirsh, Collegeville, PA (US); Steven D. Finkelmeier, Collegeville, PA (US); Robert Glinecke, Collegeville, PA (US); Luigi Martini, Harlow (GB)

(73) Assignee: Glaxosmithkline, LLC, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/197,486

(22) Filed: Aug. 3, 2011

(65) Prior Publication Data
US 2012/0029030 A1 Feb. 2, 2012

Related U.S. Application Data

(63) Continuation of application No. 11/718,154, filed as application No. PCT/US2005/042086 on Nov. 18, 2005, now Pat. No. 8,022,032.

(60) Provisional application No. 60/631,932, filed on Nov. 30, 2004, provisional application No. 60/629,876, filed on Nov. 19, 2004.

(51) Int. Cl.
*A61K 38/00* (2006.01)
*A61K 31/41* (2006.01)
*A61K 31/40* (2006.01)

(52) U.S. Cl. ............ 514/1.1; 514/360; 514/423

(58) Field of Classification Search ............ 514/1.1, 514/360, 423
See application file for complete search history.

(56) References Cited

U.S. PATENT DOCUMENTS

| | | |
|---|---|---|
| 3,547,682 A | 12/1970 | Erb |
| 3,809,289 A | 5/1974 | Komendowski |
| 4,028,024 A | 6/1977 | Moreland |
| 4,425,181 A | 1/1984 | Bahr |
| 4,571,924 A | 2/1986 | Bahrani |
| 4,738,724 A | 4/1988 | Wittwer et al. |
| 4,738,817 A | 4/1988 | Wittwer et al. |
| 4,938,080 A | 7/1990 | Sarrine et al. |
| 5,074,426 A | 12/1991 | Goodhart et al. |
| 5,277,341 A | 1/1994 | Privas |
| 5,320,853 A | 6/1994 | Noda et al. |
| 5,348,062 A | 9/1994 | Hartzell et al. |
| 5,360,795 A | 11/1994 | Townsend et al. |
| 5,369,940 A | 12/1994 | Soloman |
| 2,714,861 A | 8/1995 | Castronuovo |
| 5,443,459 A | 8/1995 | Wong et al. |
| 5,443,461 A | 8/1995 | Atkinson et al. |
| 5,460,827 A | 10/1995 | Sanderson et al. |
| 5,505,957 A | 4/1996 | D'Angelo et al. |
| 5,508,040 A | 4/1996 | Chen |
| 5,609,010 A | 3/1997 | Sauter |
| 5,672,359 A | 9/1997 | Digenis et al. |
| 5,674,530 A | 10/1997 | Amidon et al. |
| 5,756,117 A | 5/1998 | D'Angelo et al. |
| 5,824,338 A | 10/1998 | Jacobs et al. |
| 5,932,240 A | 8/1999 | D'Angelo et al. |
| 5,966,910 A | 10/1999 | Ribani et al. |
| 6,010,706 A | 1/2000 | Candau et al. |
| 6,108,030 A | 8/2000 | Yamamoto et al. |
| 6,126,767 A | 10/2000 | Smith et al. |
| 6,170,152 B1 | 1/2001 | Ohta et al. |
| 6,280,771 B1 | 8/2001 | Monkhouse et al. |
| 6,482,433 B1 | 11/2002 | DeRoos et al. |
| 6,514,518 B2 | 2/2003 | Monkhouse et al. |
| 6,561,977 B2 | 5/2003 | Williams et al. |
| 6,591,585 B2 | 7/2003 | Stolz |
| 6,772,026 B2 | 8/2004 | Bradbury |
| 6,799,413 B2 | 10/2004 | Aylward |
| 6,916,483 B2 | 7/2005 | Ralph et al. |
| 6,960,357 B2 | 11/2005 | Chopra |
| 7,056,534 B2 | 6/2006 | Christenson et al. |
| 8,022,032 B2 * | 9/2011 | Kirsh et al. .................. 514/1.1 |
| 2002/0018816 A1 | 2/2002 | Monkhouse et al. |
| 2003/0003151 A1 | 1/2003 | Chopra |
| 2003/0074234 A1 | 4/2003 | Stasny |
| 2003/0194431 A1 | 10/2003 | Miller et al. |
| 2003/0200726 A1 | 10/2003 | Rast |
| 2004/0013703 A1 | 1/2004 | Ralph et al. |
| 2004/0022852 A1 | 2/2004 | Chopra |
| 2004/0126422 A1 | 7/2004 | Tony Yu et al. |
| 2004/0137062 A1 | 7/2004 | Chopra |
| 2004/0156903 A1 | 8/2004 | Abrams et al. |
| 2004/0181429 A1 | 9/2004 | Shannon |
| 2004/0181528 A1 | 9/2004 | Tirinato et al. |

(Continued)

FOREIGN PATENT DOCUMENTS

| | | |
|---|---|---|
| EP | 1382321 | 1/2004 |
| JP | 9221416 | 8/1997 |

(Continued)

OTHER PUBLICATIONS

Written Opinion for Singapore Application No. 2008-03605-5 dated Jan. 4, 2010.
International Search Report/Written Opinion dated Oct. 1, 2007 and International Preliminary Report on Patentability (IPER) dated Nov. 17, 2010 for PCT/US2006/061032.
Official Actions for Russian Application No. 2007122763/15 (024795) dated Oct. 9, 2009 and Jun. 22, 2010.

(Continued)

*Primary Examiner* — Raymond Henley, III
(74) *Attorney, Agent, or Firm* — Ohlandt, Greeley, Ruggiero & Perle, LLP

(57) ABSTRACT

Generally the method involves identifying the concentration of each of two or more active therapeutics tailored to treat a particular patient's unique metabolism and one or more diseases, communicating that information to a producer who has multiple fixed or variable concentrations of each active available, where the producer then combines the individual concentrations of each active into single units such as a tablets or pills, and distributes those indirectly or directly to the patient.

10 Claims, 5 Drawing Sheets

U.S. PATENT DOCUMENTS

| | | | |
|---|---|---|---|
| 2004/0200043 A1 | 10/2004 | Wong et al. |
| 2004/0242454 A1 | 12/2004 | Gallant |
| 2004/0243481 A1 | 12/2004 | Bradbury et al. |
| 2004/0253312 A1 | 12/2004 | Sowden et al. |
| 2005/0038504 A1 | 2/2005 | Halleriet et al. |
| 2005/0112235 A1 | 5/2005 | Shefer et al. |
| 2005/0136105 A1 | 6/2005 | Allen et al. |
| 2005/0136119 A1 | 6/2005 | Bunick et al. |
| 2005/0175696 A1 | 8/2005 | Edgren et al. |
| 2005/0208131 A1 | 9/2005 | Veilleux et al. |
| 2005/0226906 A1 | 10/2005 | Moneymaker et al. |
| 2005/0249807 A1 | 11/2005 | Brown et al. |
| 2005/0260247 A1 | 11/2005 | Ralph et al. |
| 2006/0000470 A1 | 1/2006 | Clarke et al. |
| 2006/0001866 A1 | 1/2006 | Clarke et al. |
| 2006/0002594 A1 | 1/2006 | Clarke et al. |
| 2006/0002986 A1 | 1/2006 | Clarke et al. |
| 2006/0003000 A1 | 1/2006 | Solomon et al. |
| 2006/0009385 A1 | 1/2006 | Hoffman et al. |
| 2006/0016830 A1 | 1/2006 | Clarke et al. |
| 2006/0017916 A1 | 1/2006 | Clarke et al. |
| 2006/0036368 A1 | 2/2006 | Chen et al. |
| 2006/0057200 A1 | 3/2006 | Schaeffler |
| 2006/0057201 A1 | 3/2006 | Bonney et al. |
| 2006/0062859 A1 | 3/2006 | Blum et al. |
| 2006/0068011 A1 | 3/2006 | Ebube |
| 2006/0078621 A1 | 4/2006 | Wedinger et al. |
| 2006/0078897 A1 | 4/2006 | Wedinger et al. |
| 2006/0099257 A1 | 5/2006 | Langridge et al. |
| 2006/0141001 A1 | 6/2006 | Finkelmeier et al. |
| 2006/0198850 A1 | 9/2006 | Razzak |
| 2007/0193225 A1 | 8/2007 | Bailey et al. |
| 2008/0306622 A1 | 12/2008 | Bailey et al. |
| 2009/0149507 A1 | 6/2009 | Kirsh et al. |

FOREIGN PATENT DOCUMENTS

| | | |
|---|---|---|
| JP | 2003505498 | 2/2003 |
| JP | 2003530423 | 10/2003 |
| JP | 2004041680 | 2/2004 |
| RU | 767415 | 9/1980 |
| SU | 458966 | 1/1975 |
| WO | 9511671 | 5/1995 |
| WO | 9836739 | 8/1998 |
| WO | 9959552 | 11/1999 |
| WO | 0108666 | 2/2001 |
| WO | 0112103 | 2/2001 |
| WO | 0158238 | 8/2001 |
| WO | 0164182 | 9/2001 |
| WO | 03026627 | 4/2003 |
| WO | 03041690 | 5/2003 |
| WO | 03057136 | 7/2003 |
| WO | 03086267 A2 | 10/2003 |
| WO | 03086267 A3 | 10/2003 |
| WO | 03086267 B1 | 10/2003 |
| WO | 2004091794 | 10/2004 |
| WO | 2005105038 | 11/2005 |
| WO | 2005111955 | 11/2005 |
| WO | 2006035416 | 4/2006 |
| WO | 2006055886 | 5/2006 |
| WO | 2006060445 | 6/2006 |
| WO | 2007062323 | 5/2007 |

OTHER PUBLICATIONS

V.I. Chueshov; "Industrial Technology of Medicaments" ed.; 2002; NFAU Publishers; pp. 406-408.

Shin-Estu Chemicals Co., Ltd; "Metolose"; Cellulose and Pharmaceutical Excipients Department; pp. 1-12.

Further Examination Report dated Aug. 28, 2009 for corresponding application No. 555244 in New Zealand.

International Search Report dated Jul. 14, 2006 based on corresponding PCT application No. PCT/US2005/42216.

Korzhavikh et al.; "Various Types of Tablets with a Modified Release"; No. 12; 2003; pp. 1-6 (with English Translation).

Search Report dated Oct. 5, 2006 for WO 2006/055886.

European Search Report dated Jan. 11, 2010 for European application No. 05849258.8.

Japanese Office Action dated Dec. 13, 2011 for Japanese application No. 2007-543329 (with English translation).

Japanese Office Action dated May 15, 2012 for Japanese application No. 2007-543329 (with English translation).

\* cited by examiner

METHOD FOR CUSTOMIZED DISPENSING OF VARIABLE DOSE DRUG COMBINATION PRODUCTS FOR INDIVIDUALIZING OF THERAPIES

CROSS-REFERENCE TO RELATED APPLICATIONS

The present application is a continuation of U.S. patent application Ser. No. 11/718,154, filed on Apr. 27, 2007, now U.S. Pat. No. 8,022,032, issued on Sep. 20, 2011, which is in turn a 35 U.S.C. §371 application of International Application No. PCT/US2005/042086, filed on Nov. 18, 2005, which in turn claims the benefit of U.S. Provisional Application Nos. 60/631,932, filed on Nov. 30, 2004, and 60/629,876, filed on Nov. 19, 2004.

FIELD OF THE INVENTION

This invention relates to a method for providing individualized, customized, combined doses of two or more drugs to an individual. Generally the method involves manufacturing a series of drug formulations in physical forms which can be combined, stockpiling those forms identifying the concentration of each of two or more active therapeutics tailored to treat a particular patient's unique metabolism and one or more diseases, communicating that information to a producer who has multiple fixed or variable concentrations of each active available, where the producer then combines the individual concentrations of each active into single units such as a tablets or pills, and distributes those indirectly or directly to the patient.

BACKGROUND OF THE INVENTION

Combining two or more small molecule active ingredients into one delivery system is becoming a generally accepted approach to providing enhanced treatment of certain diseases, or as a method for increasing compliance with or timelier uptake of a second drug which complements the first active. Currently these combinations are manufactured by a pharmaceutical company as a unitary pill or tablet with fixed concentrations of each drug and sent to a distributor. The distributor then ships supplies of each finished product to a dispensing group such as a pharmacy. Then, based on a script written by a healthcare provider or under the direction of a healthcare provider, the pharmacy dispenses these tablets, pills, ointments, and the like to the patient.

Examples of binary systems can be found amongst the prescription drug listings of currently market products and in over-the-counter products as well. Fixed dose prescription drug combinations are available for treating respiratory diseases, type 2 diabetes, AIDS, and certain psychiatric disorders. And there is a growing number of binary combinations being proposed, undergoing clinical studies, or in pre-market approval review by regulatory agencies. Examples are fixed dose combinations for treating cardiovascular diseases. Recently some have proposed a so called "poly pills" combining up to 6 actives for reducing cardiovascular diseases in at-risk people, especially amongst older populations. And vaccine manufacturers have been providing clinicians with preparations which contain up to 4 components in a single dose.

For treating asthma, one example of a fixed dose combination is Advair Disckus® sold by GlaxoSmithKline. It is a combination of an inhaled steroid, fluticasone propionate, and a long-acting beta agonist, salmeterol, both of which were previously market separately for treating asthma. It is marketed as a dry powder dispensed via an oral inhaler and is available in 3 fixed dose combinations of fluticasone propionate/salmeterol: 100 mcg/50mcg, 250 mcg/50 mcg and 500 mcg/50 mcg.

For treating type 2 diabetes, an example is Avandament®, also sold by GSK. It combines rosiglitazone maleate, a member of the thiazolidinedione (TZD) class, and metformin hydrochloride, a member of the biguanide class in a single tablet. Rosiglitazone directly targets insulin resistance, a major underlying cause of type 2 diabetes, whereas metformin acts primarily by decreasing the production of sugar by the liver. Avandamet is available in fixed dose combinations for oral administration as tablets containing rosiglitazone maleate and metformin hydrochloride equivalent to: 1 mg rosiglitazone with 500 mg metformin hydrochloride (1 mg/500 mg), 2 mg rosiglitazone with 500 mg metformin hydrochloride (2 mg/500 mg), 4 mg rosiglitazone with 500 mg metformin hydrochloride (4 mg/500 mg), 2 mg rosiglitazone with 1,000 mg metformin hydrochloride (2 mg/1,000 mg), and 4 mg rosiglitazone with 1,000 mg metformin hydrochloride (4 mg/1,000 mg).

In the treatment of psychiatric illnesses, Lilly sells Symbyax® which is a fixed dose combination of olanzapine and fluoxetine HCl. It is the first drug-based treatment for treating bipolar depression. It is available as tablets in fixed doses of olanzapine/fluoxetine HCL: 6 mg/25 mg, 6 mg/50 mg, 12 mg/25 mg, and 12 mg/50 mg.

Binary cardiovascular drug combinations are another fertile area for investigating the benefits of multiple actives in 1 pill. Statins in combination with a drug for treating another disease associated with a cardiovascular risk factor, or other drugs also useful for treating hyperlipidemea are receiving a good deal of attention. Merck is combining simvastatin (Zocor®) with Schering-Plough's ezetimibe (Zetia®) which blocks the absorption of cholesterol in the intestines to treat abnormal lipid levels in humans. Pfizer has plans to combine atorvastatin (Lipitor®) with a long-acting calcium channel blocker amlodipine besylate (Norvasc®) a blood-pressure drug. NSAID/statin combinations are also being proposed, as exemplified by the clinical trials in progress looking at the effectiveness of combining aspirin and pravastatin.

AIDS treatment has also seen combination products, particularly that of Combivar® which is comprised of two synthetic nucleoside analogs lamivudine and zidovudine. It is a GlaxoSmithKline product.

Vaccines for bacterial and viral infections are now available as 3 or 4 component systems. For diphtheria, tetanus and pertussis there are vaccines which contain 3 components in a single shot, the so-called DTaP vaccines. Vaccination against three common childhood diseases, measles, mumps and rubella can be done with a so-called MMR vaccine. In another instance, the vaccine Infanrix IPV (GSK Biologicals) can provide enhanced immunity against measles, mumps and rubella, and poliomyelitis.

A "Polypill" has been proposed for treating cardiovascular risk [*British Medical Journal* (vol 326, p 1419, 1423, and 1427)]. As proposed it would contain a cocktail of six existing drugs to address to try to lower the four key risk factors for heart disease: cholesterol, high blood pressure, high homocysteine blood levels and blood platelet function. In the polypill proposal, a statin would be included to reduce high levels of the "bad" LDL cholesterol, slashing the risk of heart disease, while three blood pressure lowering drugs would reduce stroke risk. Folic acid would be included to cut high homocysteine levels, which can encourage the build up of fatty plaques in arteries. And finally aspirin would be added to regulate the function of blood platelets. This polypill would be a fixed dose combination. It has received mixed reviews. "It's not totally a bad idea," says Dr Robert Bonow of the American Heart Association. "Cardiovascular disease is the leading cause of death worldwide, and we're not going to be able to do enough angioplasties to treat entire populations." But he worries that packaging six drugs in a single, one-size-fits-all pill carries the twin dangers of unnecessary side effects for people at low risk, and, conversely, under treating those who need more aggressive care. Along similar lines, an article in the Wall Street Journal Europe titled: "Drug Makers Offer Patients Two Pills in One" (10 Nov. 2004) noted that doctors are inclined to avoid combination drugs because they are only available currently as fixed-dose in a limited number of doses, making it difficult to customize treatment regimens or to address problems patients may have with the fixed-dose approach. A doctor Yacht was quoted as saying: "If a patient has side effects on a combination, I don't know what's causing them".

This invention provides a way to obviate or mitigate the risks associated with a one-size-fits-all multiple component approach manufactured by a pharmaceutical company by giving the healthcare provider an opportunity to choose from a set of actives, select a concentration for each active from a broad range of pre-prepared strengths, and have them combined into a single formulation, a customized formulation if you will. This allows individualizing drug treatment to meet the needs of each patient based on his or her unique metabolism, current health status and medical condition.

SUMMARY OF THE INVENTION

This invention relates to a method for providing custom drug and nutritional therapies for preventing or treating diseases comprising at least two or more of the following steps, the steps comprising:
  a) manufacturing a series of drug or nutritional formulations in physical forms which can be combined into a final preparation and which have varying concentrations of said drug or nutritional supplement;
  b) stockpiling these formulations with a group which has the capacity to combine the physical forms into a finished product;
  c) identifying two or more drugs and/or nutritional supplements and the concentration from the series tailored to treat a particular patient's unique metabolism and one or more diseases which the patient may suffer from or is suffering from and which can be prevented by or treated by the identified drugs and/or nutritional supplements identified;
  d) communicating that information to the group stockpiling said formulations;
  e) wherein the group combines the physical forms of the identified drugs and/or supplements into single units, and
  f) distributing said single units indirectly or directly to the patient.

In a related aspect this invention relates to a method for providing custom drug and nutritional therapies for preventing or treating diseases comprising at least two or more of the following steps, the steps comprising:
  a) manufacturing a series of drug or nutritional supplement formulations in physical forms which can be combined into a final preparation and which have varying concentrations of said drug or nutritional supplement;
  b) stockpiling these formulations;
  c) identifying two or more drugs and/or nutritional supplements and the concentration from the series tailored to treat a particular patient's unique metabolism and one or more diseases which the patient may suffer from or is suffering from and which can be prevented by or treated by the identified drugs and/or nutritional supplements identified;
  d) communicating that information to the group stockpiling said series of formulations;
  e) shipping the identified series of formulations to a second group which can combine the physical forms into a final preparation; and
  f) distributing said single units indirectly or directly to the patient.

DETAILED DESCRIPTION OF THE INVENTION

Figure 1:
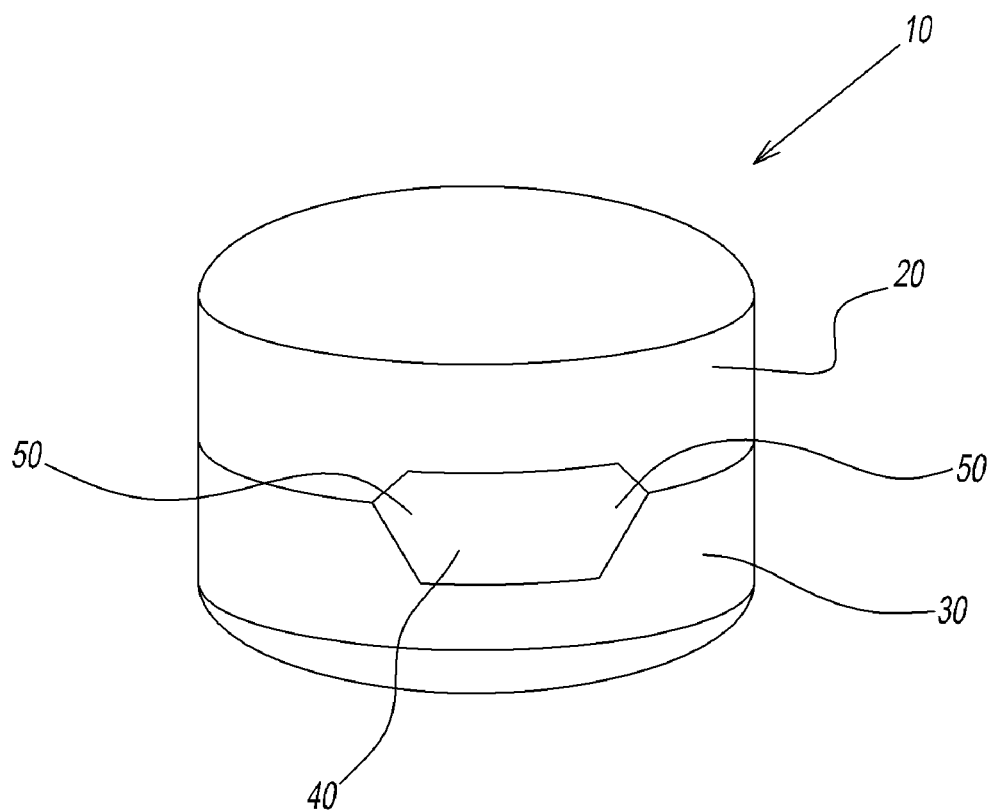
FIG. 1 is a perspective view of an embodiment of a tablet useful in the present invention.

Medical therapy is moving towards treatment of disease polypharmaceutically. In order to simplify this, many approaches have been designed to create fixed dose combination (FDC) products where the drug and dose are predetermined in the formulation based on traditional clinical studies. In this invention we describe a concept for the design and use of variable dose combination products that allow therapy to be individualized and customized, based on a healthcare provider's assessment of the patient's genetic makeup and how that may affect a particular course of available drug therapy or nutritional supplementation, current medical condition, and treatment needs and limitations of a possible treatment regimen. The process will be of use in all areas of disease management including for example, psychiatry, neurology, metabolic disease, urology, cardiovascular, oncology, pulmonary gastroenterology, rheumatology and pain management. In addition it will allow the treatment of co-morbid stages, such as depression in breast cancer, with single therapies selected by the attending physician. The concept also offers advantage in improving compliance in all therapeutic areas by minimizing the burden of taking two or more pills, a fact of life not infrequently associated with effective therapies.

In its broadest application, this process may be applied to solid, creams and gels, or liquid preparations, and in limited instances even to gases used in therapy. One can prepare solid/solid formulations, mixtures of liquids or even solid/liquid preparations. Its greatest application may be in solid tablet and pill preparations and gelatine capsule-like preparations, due to ease of custom manufacturing. Immediate release and delayed release preparations can be utilized, either individually or in combination. So in one embodiment, two immediate release preparations can be combined into one single product. In another instance an immediate release pill-like preparation containing one active can be combined with a delayed release pill-like preparation containing a second, different, active. Or two or more delayed release preparations may be combined, each containing a different active. Also, two immediate release preparations can be combined with a third immediate release preparation or a delayed release preparation. Other combinations of immediate/delayed release are within the scope of this invention.

The concept of variable combination therapies can be achieved, for example for solids, by manufacturing dosage forms in shapes and concentrations that may be used independently as single products or that, based on healthcare provider's assessment are then be assembled into a final product based on the instructions of a healthcare provider if the drugs are dispensed pursuant to a script. These dosage forms can contain 1, 2 or more actives, though the simplest case, 1 active per form, is easiest to do when it comes to managing inventory and having the flexibility to respond to a broad range of combinations in a finished preparation. These dosage forms are then ware-housed and, on demand, assembled into a single unit dose using one or more of the numerous designs and techniques available in the patent and formulation literature. Two examples of solid preparations are pills or tablets using a snap lock technique and combinations of gelatine capsules into a single capsule. Alternative biocompatible gluing processes can be used to bind together individual components. Once the combination product is ingested the tablet dissociates into the separate component tablets and behaves as independent units. The manufacturer can be any one in the chain of drug production and distribution starting with the drug manufactures an intermediate supply house, a pharmacy benefits management company, or a pharmacy such as a large mail order pharmacy, an internet pharmacy, retail chains, hospital or clinic pharmacies or independent pharmacies, or some other system for dispensing drugs directly to patients.

Variable dose combinations will offer numerous advantages over conventional fixed dose combinations. These include: flexibility for physicians to select doses, flexible dose titrations, reduced inventory requirements, improved patient compliance, improved adherence to approved therapy, reduced number of patient copays, and treatment of co-morbid therapies with single tablets. This is applicable to and number of drug products and offers the opportunity to create product families with a minimum of inventory.

Current practice in the pharmaceutical industry is for the innovator or generic house to manufacture tablets, pills, capsules, etc. It is expected this practice will be one option which can be used to create the inventory of products needed to support customizing the treatment form provided to the patient. However, the originating manufacturer of combination components is not limited to manufacturing facilities owned or controlled by innovators or generic houses. Manufacturing can be outsourced, if regulation permits. And while not much practiced now days because of controls imposed by regulatory agencies, preparations can be confected by anyone with access to and training and skills in the pharmaceutical formulation arts.

Once the variable dose combination components have been manufactured they can be warehoused, stockpiled, by the original manufacturer or shipped to and warehoused by a distributor or the group assembling the final product for transfer directly to patient; the critical issue is does the warehousing or stockpiling group have the where withal to combine components into the final preparation on demand. If not, the warehouse group can pull items from stock and ship to another who does the final assembly and then ships to the likes of a pharmacy, a healthcare provider or directly to patient. A variation on this warehousing is one where the group dispensing direct-to-patient stockpiles components and then on direction from another such as a healthcare organization, a healthcare provider, or where permitted a request from a patient. So for example it is possible that a pharmacy will stockpile components for assembly in anticipation of producing a finished product based on an authorized directive from a healthcare organization, healthcare provider or the likes of a patient-initiated refill request.

Once issues of which active, active concentration and physical form have been agreed and manufacture completed, information about these products is compiled and made available throughout the distribution chain, to healthcare providers, and optionally to patients if so permitted by law or regulation. Such information can be distributed by any convenient and efficient means depending on the particular circumstances and challenges inherent in a particular healthcare services distribution network. The data can be provided as a digital or audio file, or output to paper, as needed to meet a particular circumstance. Electronic systems provide a rapid and convenient method for distributing this information, and updating changes quickly. Maximum benefit can come from exploiting secure telecommunications technologies over dedicated telecom lines, the Internet or an extranet, or using wireless technologies. Where available, it is anticipated the information can be placed on a computer and made available to others over a telecoms network such as the Internet, or as a down-loadable file permitting transfer to another computing device such as a PC or a hand-held, e.g., cell phone or personal digital assistant.

Along with this information one can provide instructions for and tools to send requests or other information back up the distribution chain from the patient or healthcare provider to distributor to manufacturer, or any two or more of these groups. Again, paper or electronic systems can be used, but electronic systems provide the most rapid and efficient way to get information back and forth. To illustrate, a drug manufacturer can set up a web site populated information about what it is currently producing that can be used to create customized treatments. This site can be for informational purpose only or, if the manufacturer is doing the assembly of customized treatments, the site can provide for way for accepting input from healthcare provider who has authority to write scripts or otherwise authorize the manufacturer to send pills, etc, to patients, or for patients to request a refill of an existing prescription. Or the manufacturer's web site can be set up to redirect the reader to an intermediate such as a drug wholesaler or pharmacy who has the tools to compile a customized pill.

If the information is online, it can be provided as a flat file, as a read-only file, or it can be provided as an interactive file. If it is provided as a read-only file, the viewer may be permitted to download or print the information, or it could be locked down in w way that interdicts further usage. One illustration of a locked file system is Adobe Acrobat's 6.0 Professional software for creating .pdf files. If interaction is permitted, the online functions can include selecting, authorizing, commenting, instructing, and the like, all with the goal in mind of effecting the final preparation and distribution of treatment to the patient via online exchanges. So for example the interface can have an information component coupled with an authorizing screen permitting access to an ordering system, akin to shopping online. In this iteration, a previously authorized healthcare provider can be given rights to select two or more active/concentration components based on the unique needs of her patient and send this data to the group assembling the final treatment, be it a manufacture or distributor who is holding those components and can assemble the final product or ships to someone who can do so, for redistribution to directly or indirectly to the patient.

A healthcare provider's interaction with the system is one of first diagnosing a patient's health status, and possibly genetic pre-disposition to certain therapies, and deciding on a course of drug or nutritional supplement therapy, if needed. Assuming some type of drug therapy or nutritional deficiency-correcting intervention is appropriate, the healthcare provider can look up what actives and concentrations may be available from manufacturers for combining into a single treatment, e.g., a pill or tablet. In its simplest and most efficient iteration, she can then go online and ask for authorization to prescribe combination therapies by providing information securely via the web site supporting her pre-existing rights to prescribe drugs in that jurisdiction. Once authorized to order online, she can select from a menu of drugs and concentrations a set of components reflecting a therapy appropriate to the patient's unique needs (age, genomics, life-style, medical history, etc.) as perceived during her assessment of the patient's current health. Her order can then be transmitted to the warehouse for final manufacture or the components pulled, shipped to another for assembly, and then distributed indirectly or directly to the patient.

Manufacturers can ship final product to an intermediary such as a bricks-and-mortar pharmacy or an online pharmacy, another authorized designate, directly to a patient, or to an automated, self-service, dispensing kiosk for direct retrieval by a patient or authorized party. Kiosks can also be used by pharmacies or other $3^{rd}$ party dispensing groups for managing inventory and controlling distribution. In this scenario, the components or final product are contained within the kiosk, on demand, either assembled by it into final product or if already in final form dispensed. Examples of kiosk-based systems for dispensing prescriptions, and which can be applied to nutritionals as well, can be found in the following U.S. Pat. Nos. 6,892,941, 6,871,783, 6,814,255, 6,814,254, 6,766,218, 6,735,497, 6,697,704, 6,611,733, 6,581,798, 6,564,121, 6,529,801, 6,352,200, and 5,838,575. In each of these numerous other patents are listed as disclosures relating to managing the dispensing of drugs, etc., via kiosks and the like.

Also, redistribution, or transfer, to patient can be effected through a surrogate such as the patient's healthcare provider or a designate authorized to act on the patient's behalf. This choice will depend on local law and regulation, and cultural preferences.

To obtain refills where the dispensing system operates on the Internet, via kiosks, or controlled computing environments such as a physician's office, patients can be pre-authorized in some manner in conjunction with their healthcare provider and the manufacturing to reorder directly online or have the product distributed to them through the party who provided the original prescription, e.g. a pharmacy. Alternatively the patient can contact his doctor's office and instruct them to authorize a refill, which the doctor's office can then do using established telecommunications links with the manufacturer or distributor.

Yet further illustrations of how this system could operate are the following:

a) The group stockpiling components assembles components into final product and transfers product to patient or patients surrogate directly or through an authorized dispensing organization or person.

b) A healthcare organization or provider communicates a prescription to a group stockpiling components who assembles final product and transfers it to patient or patient's surrogate.

c) A patient or legal surrogate communicates with a group stockpiling components, who prepare final product and transfers it directly to patient or patient's surrogate, or places it in a kiosk-like device from which the patient or an authorized party retrieves it.

The types of actives and concentrations of same that can be employed in this invention are unlimited, except by concerns arising from good medical practice constraints, and law and regulation.

As practical matter it is expected that the individual component concentration of drugs and nutritionals that will be used in this invention will parallel those developed by the innovator as stand-alone products. Usually a drug is manufactured in different strengths in order to accommodate treatment of different degrees of severity of the illness, or to accommodate age, gender and size limitations. For example, statins are provided as tablets in a range of concentrations to address the finding that certain patients need only a little and others need a lot of the drug because of a more severe case of hyperlipidemea. Or in the case of drugs for juveniles, because the patient has a much smaller body mass, the dose must be truncated to avoid overdosing the paediatric patient. Selection of specific concentrations to be manufactured as single components will depend on the outcome(s) of basic research and the development research underpinning bringing the drug to market. In the case of nutritional supplements, generally accepted use and regulation may be looked to for guidance in selecting an appropriate concentration of this type of active.

Actives include but are not limited to drugs, nutritional supplements, vaccines, gene therapies, anything that can be used in health maintenance or disease cure. To illustrate, the following is a list of currently available drugs which can be combined in two or more permutations for preventing or treating diseases:

Antivirals
Agenerase—antiretroviral, 50 mg capsule
Epivir—HIV& Hep B 150/300 mg, HBV 400 mg chronic Hepatitis B virus for HIV epivir+retrovir
Epzicom—HIV, 600 mg abacavir, 300 mg lamividine+$3^{rd}$. drug (Retovir)=Trzivir
Abacavir, lamivadine, zidovidine or stavidine
Zidovidine, lamividine, didanosine
Tenofovir, didanosine
Stavidine, didanosine
Lexiva—1400 mg BID, +Rilonavir 100 mg and 200 mg
Retrovir—300 mg BID
Telzir—HIV, 100 mg, w/low dose ritonavir or combination of Telzir+lopinavir+ritonavir
Trizivir—1 tablet BID, abacavir (Ziagen), lamividine (Epivir), Zidovidine (Retrovir)
Valtrex—Herpes, 500, 1000 mg
Zovirax—herpesvirus, 200 mg capsule, 400 and 800 mg tablet
Ziagen—HIV 300 mg abacavir systemic
Antibiotics
Albenza—broad spectrum anthelmintic 200 mg (destroys worms)
Amoxil 500/875 mg w/clarithromycin+lanaoprazole, omeprazole 20 mg bid, 500 mg amox qid, metronidzole 250 mg qid for Helicobacter pylori
Augmentin—375, 625 mg tablets, Pediatric dose 156 mg or 312 mg Ceftin—antibiotic 250 mg or 500 mg tablet+doxycycline for late stage lyme
Floxapen—antibiotic ideal for dialysis patients or post surgery, 250 and 500 mg capsule
Darprim—acute malaria w/sulfadonine, 25 mg tablet scored
Grisovin—antifungal for ringworm where ointment is ineffective
Halfan—antimalarial 250 mg tablet—interacts with drugs that prolong QTc
Malarone—antimalarial taken for 3 days, followed by 30 mg pimaqine, 250 mg atovquone, 100 mg poquanil, Pediatric dose followed by 62.5 mg atovquone, 25 mg poquanil
Septrin—antibiotic sulphanothoxazol/trimethoprim,
Oncology
Alkeran—myeloma (reduce bone marrow cells), ovarian adenocarcinoma, 2 mg uptitrate w/prednisone
Hycamtin—ovarian cancer
Leukeran—leukemia, lymphoma, 2 mg
Lanvis—acute leukaemia, 40 mg tablet
Throquanise—nonlyphocytic leukemia, 40 mg
Zofran—prevents nasea, vomiting associated w/chemotherapy
Psychiatry
Eskalith—450 mg SR, inaction with Nsaids and Cox2
Parnate—major depression w/o melancholia, 10 mg (brooding on one subject)
Paxil
Wellbutrin
Lamictal
Thorazine—antipsychotic, 10, 25, 50, 100, 200 mg tablet
Zyban—bupropion smoking cessation 150 mg
GI
Zyloric—recommended dose for gout 100 mg-600 mg, comes as 100 mg & 300 mg
Lotronex—0.5 and 1.0 mg Irritable bowel Syndrome
Pylorid—anti helicobacter pylori w/antibiotic
Tagamet—H2 antagonist, 300, 400, 800 mg tablet
Zantac—duodenal/gastic ulcers, 25, 150 mg tablet
Entereg—post operative ileus,nuopiod receptor antagonist, pain relief w/o constipation (Alvimopan)
Pain
Amerge—migraine headaches, 1 mg BID prophylactically for migraine, 2.5 mg UID or BID for cluster headaches
Amerge+599—possible application for nausea
Amerge+Zofran—possible application for nausea
Relafen—pain, arthritis, 500 mg and 750 mg
Imitrex—migraine, 35, 70, 140 mg
Urology
Doralese—benign prostatic hyperplasia, 20 mg up to 100 mg (20 mg×5)
Doralese+Verdanifl—hair growth w/o erectile dysfunction
Dutasteride/tamsulosin—BPH combo
CNS
Requip—Parkinson's, restless leg
Skeletal
Boniva—osteoporosis, 2.5 mg tablets
Diabetic
Avandia—rosiglitazone, type II, 4, 8 mg
Avandamet—metformin, >1,000 mg, (0.1-8 mg rosiglitazone combo)+glibenclamide,acarbase, sulphonylurea
Cardiac
Lanoxin—cardiac gicosids (digoxin) 125 mcg and 250 mcg+ coreg UID=14-16% peak/trough conc;
Coreg—3.125, 6.25, 12.5, 25, 50 mg+cimetidine AUC steady state by 30% w/no change in Cmax and combination of antihypertensives esp. thiazide type diruretics
Dyzade—hydochlorothizide/tranterese+coreg Antirejection
Imuran—immunosuppressive for organ transplant, ideal w/cortcosteriods
Pulmonary
Volmax—nocturnal asthma, 4 & 8 mg
Musculoskeletal & Pain Medications

| | |
|---|---|
| diclofenac | potassium |
| diclofenac | sodium |
| etodolac/XL | |
| ibuprofen | |
| ketoprofen | |
| nabumetone | |
| naproxen/sodium | |
| oxaprozin | |
| piroxicam | |
| salsalate | |
| sulindac | |

Skeletal Muscle Relaxers

| | |
|---|---|
| Dantrium | (dantrolene) |
| Flexeril | (cyclobenzaprine) |
| Lioresal | (baclofen) |
| Norflex | (orphenadrine) |
| Parafon Forte | (chlorzoxaxone) |
| Robaxin | (methocarbamol) |
| Skelaxin | (Metaxalone) |
| Soma | (carisoprodol) |
| Zanaflex | (tizanidine) |
| baclofen | |
| chlorzoxazone | |
| cyclobenzaprine | |
| methocarbamol | |

Long Acting Opiods

| | |
|---|---|
| Avinza | (morphine sulfate ER) |
| Duragesic | (transdermal fentanyl) |
| Kadian | (morphine SR) |
| Levo-Dromoran | (levorphanol) |
| MS Contin | (morphine SR) |
| Oxycontin | (oxycodone ER) |
| levorphanol | |
| methadone | |
| morphine | SR |

Drugs to treat headaches (Triptans)

| | |
|---|---|
| Amerge | (almotriptan) |
| Axert | (naratriptan) |
| Frova | (frovatriptan) |
| Imitrex tablets | (sumatriptan) |
| Maxalt MLT | (rizatriptan) |
| Zomig/ZMT | (zolmitriptan) |
| Imitrex Injection | (sumatriptan) |
| Imitrex Nasal Spray | (sumatriptan) |
| Maxalt | (rizatriptan) |

Diabetes & Endocrine Drugs

| | |
|---|---|
| Amaryl | (glimeperide) |
| Diabenese | (chlorpropamide) |
| DiaBeta | (glyburide) |

-continued

| | |
|---|---|
| Glucotrol | (glipizide) |
| Glynase | (glyburide micronized) |
| Tolinase | (tolazamide) |
| Micronase | (glyburide micronized) |
| Orinase | (tolbutamide) |
| Prandin | (repaglinide) |
| Starlix | (nateglinide) |
| glyburide | |
| glipizide | |

Ace Inhibitors
captopril
enalapril
lisinopril
Altace (ramipril)
Nutritional Supplements Nutritional supplements may be incorporated into these polypill preparations. An example is folic acid and/or vitamin $B_{12}$ supplementation for reducing homocysteine blood levels, as the latter is a known risk factor for cardiovascular disease. One or both of these can be combined with one or more drugs for treating cardiovascular risk factors, such as a statin, a platelet aggregation inhibitor such as an NSAID, a drug which reduced cholesterol uptake from the gut, or a drug to control blood pressure.

Discussion of Components and Final Products

Customized, or bespoke, products can be prepared using any type and form of pharmaceutical delivery system. However, as a practical matter, solid forms are simplest and easiest to work with, and most drugs are manufactured in some solid dosage form including hard-shelled gelatine capsules. For purposes of illustrating the simple and easy, a fuller discussion of solid dosage form follows:

Pharmaceutical formulators have created a significant body of art directed to solid dosage forms for oral use. See for example multi-compartment capsules including those of the type where each compartment has different drug release characteristics or contains a different drug substance or formulation: U.S. Pat. No. 4,738,724 (Warner-Lambert), U.S. Pat. No. 5,672,359 (University of Kentucky), U.S. Pat. No. 5,443,461 (Alza Corp.), WO 9516438 (Cortecs Ltd.), WO 9012567 (Helminthology Inst.), DE-A-3727894, BE 900950 (Warner Lambert), FR 2524311, NL 7610038 (Tapanhony NV), FR 28646 (Pluripharm), US 3228789 (Glassman), and U.S. Pat. No. 3,186,910 (Glassman) among others. U.S. Pat. No. 4,738,817 discloses a multi-compartment capsule with a similar construction to those of U.S. Pat. No. 3,228,789 and U.S. Pat. No. 3,186,910 made of a water-plasticized gelatine.

Pharmaceutical dosage forms are also known which comprise a matrix of a solid polymer, in which a drug substance is dispersed, embedded or dissolved as a solid solution. Such matrixes may be formed by an injection moulding process. This technology is discussed in Cuff G, and Raouf F, Pharmaceutical Technology June 1998 p 96-106. Some specific formulations for such dosage forms are for example disclosed in U.S. Pat. Nos. 4,678,516; 4,806,337; 4,764,378; 5,004,601; 5,135,752; 5,244,668; 5,139,790; 5,082,655 among others; in which a polyethylene glycol ("PEG") matrix is used and solid dosage forms are made by injection moulding.

More particularly, see the likes of published PCT applications WO 01/08666 and WO 2004/010978.

The first application (WO 01/08666), which is incorporated herein by reference, describe a dosage form comprising two or more connected sub-units which when assembled are particularly suitable for oral dosing. More particularly the pharmaceutical dosage form there comprises a plurality of capsule compartments each bounded and physically separated from at least one adjacent compartment by a wall made of a pharmaceutically acceptable polymer material, adjacent compartments being connected together in the assembled dosage form and being retained together by the connection at least prior to administration to a patient, one or more of the compartments containing an active ingredient, and wherein the connection is provided by a weld between parts of the assembled dosage form, suitably between immediately adjacent parts.

In the assembled dosage form of that first embodiment there are at least two, for example three, such capsule compartments. Three or more such compartments may be linearly disposed in the assembled dosage form, e.g. in an arrangement comprising two end compartments at opposite ends of the line, and one or more intermediate compartments. Suitably there may be two such capsule compartments.

In a second embodiment of that invention the pharmaceutical dosage form comprises a plurality of drug-containing sub-units connected together in the assembled dosage form and being retained together by the connection at least prior to administration to a patient, at least one of the sub-units being a solid sub-unit comprising a solid matrix of a polymer which contains a drug substance, the polymer being soluble, dispersible or disintegrable in the patient's gastro-intestinal environment to thereby release the drug substance, and wherein the connection is provided by a weld between parts of the assembled dosage form.

In one form of said foregoing second embodiment all of the sub-units in the dosage form of this invention may be solid sub-units, e.g. two or more such solid sub-units, e.g. three such solid sub-units.

In another form of the second embodiment, one or more of the sub-units comprise a solid sub-unit, and one or more of the other sub-units may comprises a capsule compartment bounded by a wall made of a pharmaceutically acceptable polymer material, one or more of the said capsule compartments containing a drug substance.

As described in the WO 01/08666 specification, in the assembled dosage form there may be at least two sub-units. Such an assembled dosage form may comprise three or four sub-units comprising one, two or three solid sub-units, combined with independently one, two or three capsule sub-units. Three or more such sub-units may be linearly disposed in the assembled dosage form in an arrangement comprising two end sub-units at opposite ends of the line, and one or more intermediate sub-units. For example such an assembled dosage form may comprise a solid sub-unit connected to a capsule compartment; a solid sub-unit between two end capsule compartments; an end capsule compartment, an intermediate capsule compartment and an end solid sub-unit; an end capsule compartment, an intermediate solid sub-unit and an end solid sub-unit; or an intermediate capsule compartment between two end solid sub-units. An assembled dosage of four such sub-units may comprise two end solid sub-units, an intermediate solid sub-unit and an intermediate capsule compartment. Alternately it may comprise two end solid sub-units with two intermediate capsule sub-units, or other combinations of sub-units.

In the assembled dosage form the adjacent sub-units, whether capsule compartments, solid sub-units or combinations thereof, are connected together by means of a weld at the area where two adjacent parts of the dosage form, e.g. sub-units, are in contact, e.g. a thermal weld, an ultrasonic or inductive weld, or an adhesive weld (e.g. curable adhesives such as UV curable adhesive). A thermal weld may for example be achieved by bringing sub-units into adjacent contact and applying localised heating for example produced by directing a laser beam or a fine jet of hot gas e.g. nitrogen at the area where two adjacent sub-units are in contact. In thermal, inductive and ultrasonic welding normally localised fusion together of the materials of adjacent parts of the dosage form which are in contact occurs, and on subsequent solidification of the materials a bond is formed between the adjacent parts. An adhesive weld may be achieved by applying an adhesive (e.g. curable adhesives such as UV curable adhesive) to parts of the dosage form which when the dosage form is assembled are in contact, and then causing or allowing the adhesive to set.

The multi-component dosage form of that invention is particularly suited to fabrication using ultrasonic welding.

Ultrasonic welding is a known technique involving the use of high frequency sound energy to soften or melt a thermoplastic material at the site where a joint with the material is required. A general description of ultrasonic welding is for example to be found in the publication "Ultrasonic Welding of Thermoplastics" (TWI Ltd., Abington, Cambridgeshire G B, (1997)). Parts to be joined are held together under pressure and then subjected to ultrasonic vibrations usually at a frequency of 20-40 kHz. The actual mechanism responsible for the generation of heat at the joint site is not well understood. An ultrasonic welding machine comprises five main components, being a power supply, a control system, a welding head, a fixture to hold the parts to be welded, and a system to apply the required pressure. The power supply converts electricity into high frequency electric power which drives a transducer, e.g. a piezoelectric transducer, which converts electrical energy, e.g. from the mains supply, into mechanical, i.e. ultrasonic, energy. Between the transducer and the parts to be welded is located a booster and horn system, being a usually metallic component which serves to amplify the ultrasonic waves (the booster horn), transmit the clamping pressure, and deliver the sound energy to the part to be welded (the sonotrode or welding horn). For successful ultrasonic welding careful design of the parts to be welded and set up of the welding equipment is important.

Adjacent parts of the dosage form of that invention may have features to facilitate the connection of the parts together, particularly to assist or supplement the weld.

For example adjacent parts, e.g. sub-units, of the dosage form of it may have substantially planar regions of their surface which may be brought into contact and then the weld may be formed, or may have regions of their surface of complementary, preferably interconnecting shapes, thereby facilitating connecting sub-units together by engagement of these complementary shaped parts.

Preferably, additionally or alternatively adjacent sub-units may be provided with respectively inter-connectable first and second connectable parts such that the first connectable part on one sub-unit may connect with the second connectable part on an adjacent part of the dosage form. This interconnection may contribute to the strength of bond achieved by the weld, or additionally or alternatively may help to hold adjacent parts of the dosage form together prior to and in readiness for the weld to be formed and contributes to the retention of the adjacent sub-units together, to with via a retaining friction, snap, screw or other kind of fit between the connectable parts. The connectable parts may be such as to facilitate the assembly together of the sub-units in preferred configurations. The connectable part(s) on one or more one sub-unit may be such as to only connect with a corresponding connectable part on other selected sub-units but not with non-corresponding connectable parts on other sub-units. Alternatively the connectable parts on the sub-units may be common and interchangeable so that the sub-units may be connected together in a wide range of combinations. This means inter alia that otherwise different capsule compartments or solid sub-units may have mutually connectable parts so that the different capsule compartments or solid sub-units may be connected together in different combinations of solid sub-units or solid sub-units and capsule compartments.

In another embodiment the respective first and second connectable parts may be respectively interlocking parts. So first or second part may be a socket part, and the corresponding second or first connectable part may be a corresponding plug part which fits into the socket with a retaining friction, snap, screw or other kind of interlocking fit. If for example these plug and socket parts are common then any plug part on any solid sub-unit or capsule compartment may interconnect with any socket part on another solid sub-unit or capsule compartment.

In a friction fit for example the plug part may be slightly larger than the socket such that force needs to be applied against the natural resilience and contact friction of the plug and socket parts to cause the plug part to enter the socket, and similar force needs to be applied to separate them. In a snap fit for example the plug and socket parts may be respectively provided with a concavity and a corresponding convexity, such as a ridge and groove, which lock together as the parts are forced together against the natural resilience of the parts. Such a ridge and groove may for example comprise a co-operating circumferential or part circumferential bead and groove, for example located about the circumference of a connectable plug and socket part.

The foregoing description provides one way of preparing components and assembling them into a bespoke final product. For another way of creating components and assembling them into a final product, see the description set out in WO 2004/010978 which is incorporated herein by reference.

For yet another illustration of a means for preparing product from components, reference is made to FIGS. 1-8 attached hereto and discussed in detail below. These embodiments provide the where whit hall to produce components comprising a drug in two or more concentrations per component, and means for assembling them into a final patient product, thus delivering a plurality of active agents customized to the needs of an individual patient.

Discussion of the Drawings

Figure 2:
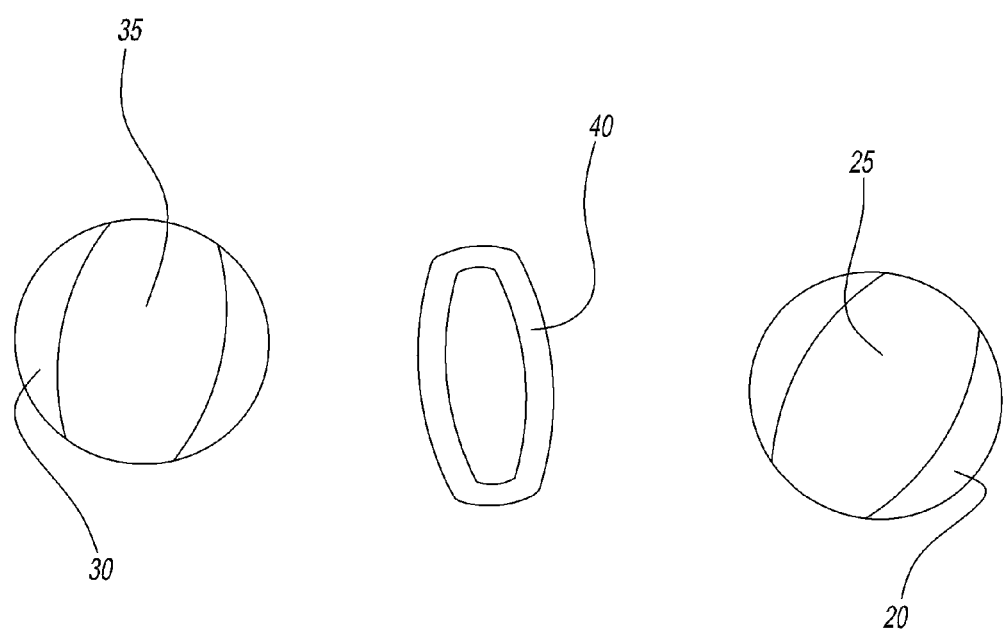
FIG. 2 is an exploded plan view of the pharmaceutical product of FIG. 2.

Referring to the drawings, and in particular FIGS. 1 and 2, a preferred embodiment of the pharmaceutical product is shown and generally referred to by reference numeral 10. Product 10 has an upper portion 20, a lower portion 30 and a middle portion 40. Upper, lower and middle portions 20, 30 and 40 form three distinct components. These components can be formed by tablet compression, although the present invention contemplates the use of other methods and processes for forming the individual components.

The upper, lower and middle portions 20, 30 and 40 can include excipients, such as within the core matrix, to control the release rates for the three portions. One or more (or none) of the upper, lower and middle portions 20, 30 and 40 can also be coated, such as by using a conventional coating process, with distinct coating systems with various functionalities to further control the rate of release of each of the three portions.

The upper, lower and middle portions 20, 30 and 40 are provided with interlocking shapes, which allow for release of the active agent from all three of the portions and which strengthens the connection between the portions. The upper, lower and middle portions 20, 30 and 40 are preferably nonreleasably connected or secured together so as to deliver multiple active agents through the use of a single delivery device or vehicle.

The upper, lower and middle portions 20, 30 and 40 can be connected through various methods, such as, for example, use of glues or adhesives, polymers, waxes; mechanical methods, structures or means; application of energy; and any combination of such methods.

The connection methods, and the components used therein, can include, but are not limited to, polymers, such as PEG or HPMC; Gelatine, such as Pharmagel; starch; gum, such as chicle, latex sap from the sapodilla tree and natural rubber; gum bases, such as natural resins, including sorva and jelutong; waxes, such as cheese wax (e.g., Paradip®), chewing gum wax (e.g., Paramelt®), butyl or polyisobutylene rubber, beeswax, carnauba Wax and microcrystalline wax (e.g., Polywax®); food grade adhesives, such as sugar-based edible adhesive; envelope grade adhesives; printed inks (as binders), such as HPMC and Shellac's; hot melt food grade glues; epoxy; opadry overcoat such as being wetted with water or alcohol (e.g., ethanol, methanol, IPA); dental adhesives; and quick dissolving or heat sensitive films.

The connection methods further include, but are not limited to, mechanical methods, such as, for example, a locking pin mechanism; a snap-fit; a screw-fit; a pressure sensitive compression; an injection moulded locking pin; banding; shrink wrapping; and injection mould glue. The connection methods further include, but are not limited to, application of energy, such as, for example, ultrasonic welding; lasers; microwaves; heat; and friction welding. Although, the present invention contemplates the use of other connection methods, structures or components that facilitate and/or strengthen the connection between the upper, lower and middle portions 20, 30 and 40.

As shown in FIG. 2, upper portion 20 has a recess 25 and lower portion 30 has a recess 35. The recesses 25 and 35 preferably extend to the periphery or outer edge of upper and lower portions 20 and 30. Recesses 25 and 35 conform to the shape of middle portion 30 so that a tight fit can be achieved between the upper, lower and middle portions 20, 30 and 40 when product 10 is assembled. In the preferred embodiment, middle portion 40 has an oval or round shape, although the present invention contemplates the use of other shapes, such as, rectangular, which can facilitate and strengthen the connection between the components. The tight fit between the upper, lower and middle portions 20, 30 and 40 strengthens the connection between the components, as well as provides a more aesthetically pleasing, unified product 10.

Middle portion 40 is narrower than upper and lower portions 20 and 30 so that an interlocking interface or boundary 50 is formed between the three portions when they are connected. The interlocking interface 50 is preferably non-linear in order to provide structural support by way of a mechanical lock being formed between the upper, lower and middle portions 20, 30 and 40. The interlocking interface 50 also increases the surface contact area between the upper, lower and middle portions 20, 30 and 40 so that there is more area for connection and a greater bond formed.

The interlocking interface 50 allows middle portion 40 to be exposed so that the middle portion is also able to release its active agent at the desired release rate. However, the present invention contemplates recesses 25 and 35 being positioned (e.g., centrally) along upper portion 20 and lower portion 30 such that when all three portions are connected, the middle portion 40 is not exposed. In such an alternative embodiment, the release of the active agent in middle portion 40 would be dependent on the deterioration of either or both of upper and lower portions 20 and 30 so that the middle portion eventually becomes exposed.

Product 10 is preferably formed through use of a rotary press to compress three distinct matrix cores in the desired shapes of the upper, lower and middle portions 20, 30 and 40. A coating pan, or other coating method or means, can coat any number of the upper, lower and middle portions 20, 30 and 40. The upper, lower and middle portions 20, 30 and 40 can be positioned together in an interlocked fashion and using a binding process, such as one of the connection methods described above, the portions can be connected into one entity or delivery vehicle.

The upper, middle and lower portions 20, 30, and 40 are independently formulated to achieve a desired rate of release, e.g., a slow-rate, a medium-rate and an instant-rate of release. As such, product 10 can deliver three separate active agents at three different rates of release. This allows product 10 to target specific areas of the gastro intestinal tract for delivery of the various active agents. In product 10, the upper portion 120 has a medium release rate, the lower portion 130 has a slow release rate and the middle portion 140 has an immediate release rate. However, the present invention contemplates the use of other release rates for one or more the components of product 10 or any of the other embodiments that are described herein.

Product 10 provides for multiple active agents that are independent of each other in a single entity to achieve a combination therapy product. The coating on one or more (or none) of the upper, lower and middle portions 20, 30 and 40 further provides for control of the release rates of the active agents. The use of three distinct components for upper, lower and middle portions 20, 30 and 40, in combination with the coating of each of the components, allows product 10 to provide for six different modes of release at the various stages of the GI tract. Additionally, incompatible active agents can still be delivered through use of a single vehicle, i.e., product 10.

Figure 3:
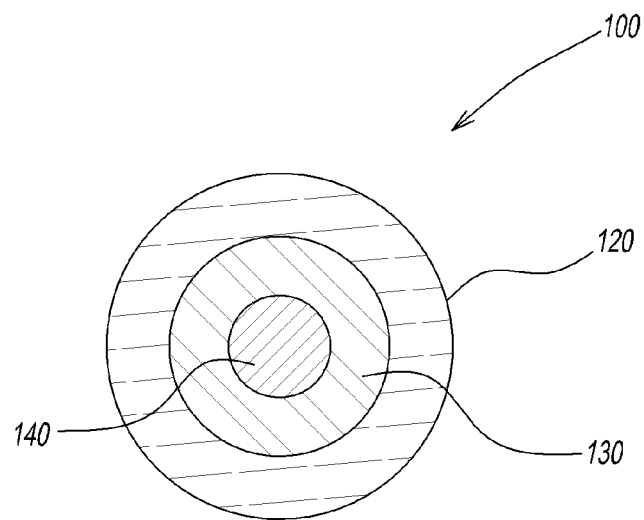
FIG. 3 is a plan view of an alternative embodiment of the pharmaceutical product of the present invention.
Figure 4:
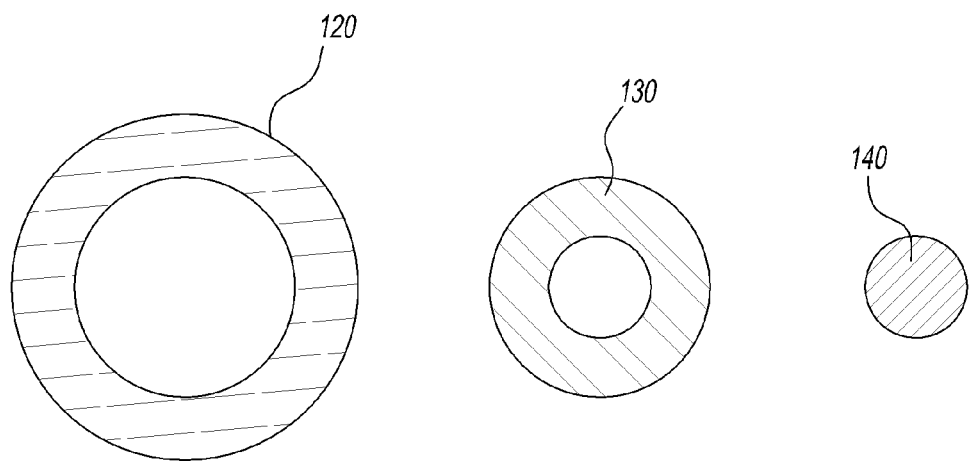
FIG. 4 is an exploded plan view of the pharmaceutical product of FIG. 4.

Referring to FIGS. 3 and 4, a second embodiment of the pharmaceutical product is shown and generally referred to by reference numeral 100. Product 100 has an outer portion 120, an intermediate portion 130 and an inner portion 140 that form three distinct components, which can be formed by tablet compression.

Similar to product 10, the outer, intermediate and inner portions 120, 130 and 140 can include excipients to control the individual release rates and can also be coated to further control the release rates. The outer, intermediate and inner portions 120, 130 and 140 are concentrically aligned when connected or assembled, with the tops and bottoms of the intermediate and inner portions remaining exposed, which allows for release of the active agent for all three of the portions. The concentric alignment of the outer, intermediate and inner portions 120, 130 and 140 increases surface area there between, which strengthens their connection.

The outer, intermediate and inner portions 120, 130 and 140 can be connected through various methods, such as, for example, glues or adhesives; polymers; waxes; mechanical methods, structures or means; by application of energy; and any combination of such methods, including the methods described above with respect to product 10 and/or other methods, structures or binding ingredients that facilitate or strengthen the connection between the portions.

The outer, intermediate and inner portions 120, 130 and 140 are independently formulated to achieve a desired rate of release, e.g., a medium rate, a slow rate and an immediate rate, and are each compressed to make the desired ring or donut-like shape for the outer and intermediate portions and the cylindrical shape for the inner portion. The outer, intermediate and inner portions 120, 130 and 140 can be coated with a functional coating system to further control the rate of release and the three components are interlocked together in a concentric alignment. In product 100, the inner portion 140 has an immediate release rate, the intermediate portion 130 has a medium release rate and the outer portion 140 has a slow release rate. The present invention also contemplates the use of other release rates.

Figure 5:
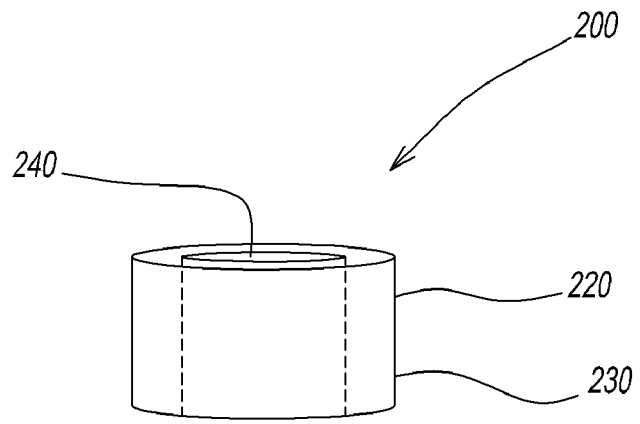
FIG. 5 is a perspective view of another alternative embodiment of the pharmaceutical product of the present invention.
Figure 6:
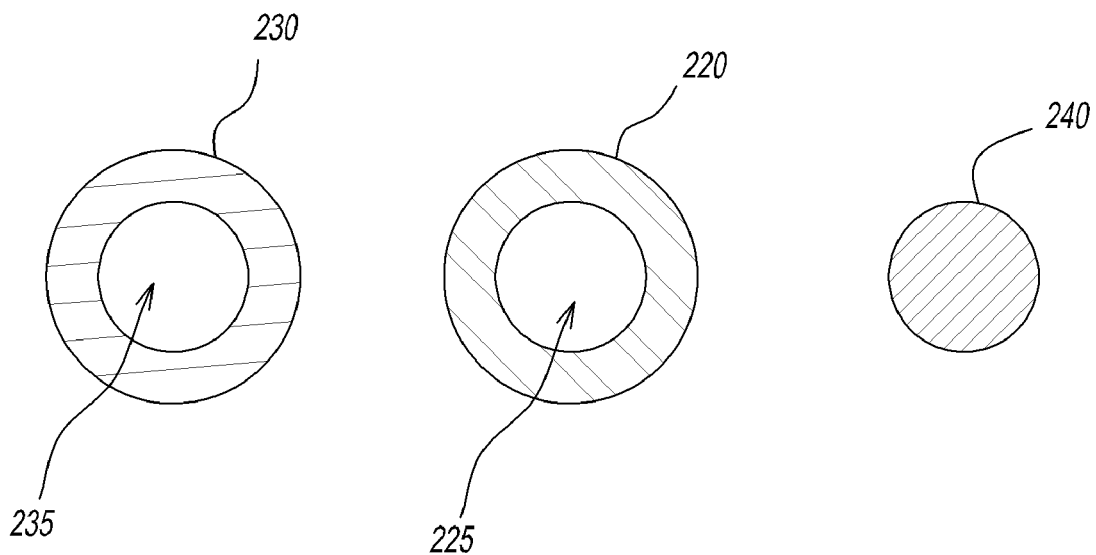
FIG. 6 is an exploded plan view of the pharmaceutical product of FIG. 6.

Referring to FIGS. 5 and 6, a third embodiment of the pharmaceutical product is shown and generally referred to by reference numeral 200. Product 200 has an upper portion 220, a lower portion 230 and an inner portion 240 that form three distinct components, which can be formed by tablet compression.

Similar to products 10 and 100, the upper, lower and inner portions 220, 230 and 240 can include excipients to control the release rates and can also be coated to further control the release rates. The upper portion 220 is seated upon the lower portion 230, while the inner portion 240 is positioned in the central holes 25 and 35 of the upper and lower portions. The upper, lower and inner portions 220, 230 and 240 all remain exposed, which allows for release of the active agent for all three of the portions.

The upper, lower and inner portions 220, 230 and 240 can be connected through various methods, such as, for example, glues or adhesives; polymers; waxes; mechanical methods, structures or means; by application of energy; and any combination of such methods, including the methods described above with respect to product 10 and/or other methods, structures or binding ingredients that facilitate or strengthen the connection between the portions.

The upper, lower and inner portions 220, 230 and 240 are independently formulated to achieve a desired rate of release, e.g., a medium rate, a slow rate and an immediate rate. Each of the upper, lower and inner portions 220, 230 and 240 are compressed to make the desired ring or donut-like shapes for the upper and lower portions and the cylindrical shape of the inner portion, which allows for the alignment of the three portions. The upper, lower and inner portions 220, 230 and 240 can be coated with a functional coating system to further control the rate of release and the three components are interlocked together. In product 200, the inner portion 240 has an immediate release rate, the lower portion 230 has a medium release rate and the upper portion 240 has a slow release rate. Although, the present invention contemplates the use of other release rates for the different components.

Figure 7:
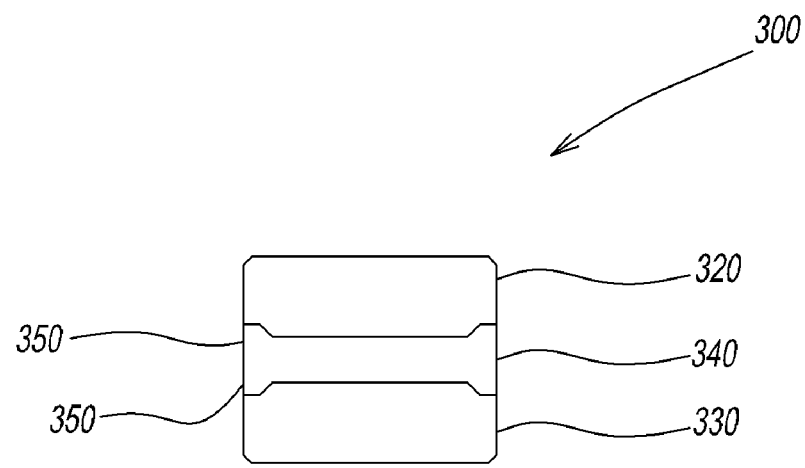
FIG. 7 is a plan view of another alternative embodiment of the pharmaceutical product of the present invention.
Figure 8:
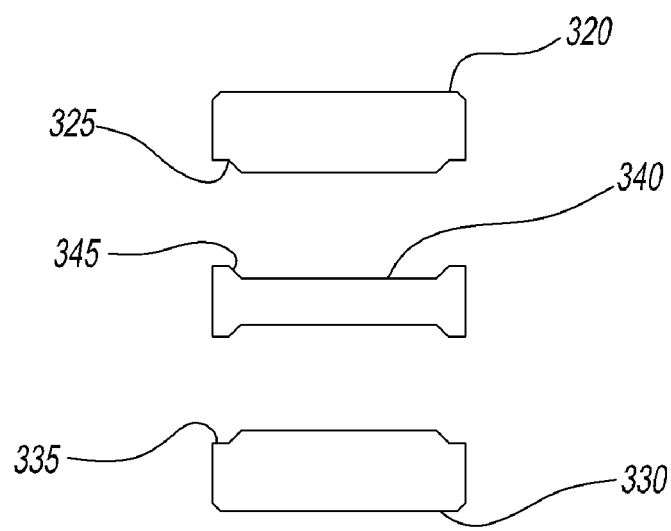
FIG. 8 is an exploded plan view of the pharmaceutical product of FIG. 8.

Referring to FIGS. 7 and 8, a fourth embodiment of the pharmaceutical product is shown and generally referred to by reference numeral 300. Product 300 has an upper portion 320, a lower portion 330 and a middle portion 340 that form three distinct components, which can be formed by tablet compression.

Similar to products 10, 100 and 200, the upper, lower and middle portions 320, 330 and 340 can include excipients and can also be coated to control the release rates of their respective active agents. The upper portion 320 is seated upon the middle portion 340, which is seated upon the lower portion 330. The upper, lower and middle portions 320, 330 and 340 all remain exposed, which allows for release of the active agent for all three of the portions.

The upper, lower and middle portions 320, 330 and 340 can be connected through various methods, such as, for example, glues or adhesives; polymers; waxes; mechanical methods, structures or means; by application of energy; and any combination of such methods, including the methods described above with respect to product 10 and/or other methods, structures or binding ingredients that facilitate or strengthen the connection between the portions.

The upper, lower and middle portions 320, 330 and 340 are independently formulated to achieve a desired rate of release, e.g., a medium rate, a slow rate and an immediate rate, and are each compressed to make the desired interlocking shapes that provide for alignment of the three portions. Middle portion 340 has male mating structures or ridges 345 along its edges while upper and lower portions 320 and 330 have female mating structures or ridges 325 and 335 along their edges. The male and female mating structures 325, 335 and 345 form an interlocking interface or boundary 350 when the upper, lower and middle portions 320, 330 and 340 are stacked upon each other and connected.

The interlocking interface 350 is preferably non-linear in order to provide structural support by way of a mechanical lock being formed between the upper, lower and middle portions 320, 330 and 340. The interlocking interface 350 also increases the surface contact area between the upper, lower and middle portions 320, 330 and 340 so that there is more area for connection and a greater bond formed. The male and female mating structures 325, 335 and 345 also provide for self-centering of the upper, lower and middle portions 320, 330 and 340 which further facilitates the manufacturing of product 300.

During the manufacturing process, the upper, lower and middle portions 320, 330 and 340 can be coated with a functional coating system to further control the rate of release and the three components are interlocked together. In product 300, the middle portion 340 has an immediate release rate, the lower portion 330 has a slow release rate and the upper portion 340 has a medium release rate. However, the present invention contemplates the use of other release rates for one or more of the components of product 300.

While each of products 10, 100, 200 and 300 provide for three separate components, the present invention contemplates the use of any number of components that are interlocked to provide for a single delivery vehicle for a plurality of active agents. It should be understood that the present invention is not limited by the type or form of active agent or the type or form of pharmaceutical or pharmaceutical-like product.

Products 10, 100, 200 and 300 have particular interlocking shapes, which facilitate the formation of the resulting single delivery entity or vehicle. However, the present invention contemplates the use of other interlocking shapes for the plurality of components, as well as other shapes of the resulting product, which allow for the delivery of a plurality of components in a single delivery vehicle, such as, for example, a snap structure, a screw structure or a pin-locking structure.

The present invention contemplates a delivery vehicle or entity having a plurality of components that are selectively connectable to each other, such as, for example, by releasable snap-fit or some other releasable connection. The present invention further contemplates a delivery vehicle or entity having a plurality of components that are selectively connected through use of a non-releasable connection, such as, for example, a non-releasable snap-fit.

Products 10, 100, 200 and 300 are preferably assembled and connected by an automated interlocking process. The binding or connection process, including the speed of the process, allows for the manufacture of the final dosage form at commercial processing rates. The compression process used in the formation of products 10, 100, 200 and 300, as well as the shapes generated, interlock in a way that they preferably appear as one entity or delivery vehicle.

Products 10, 100, 200 and 300 are manufactured through use of compression to form the individual components. However, the present invention contemplates formation of the different components by other methods as well. By forming this multi-component tablet (e.g., three distinct components that form one multi-functional product), the final dosage form can have up to 6 possible modes of release (and more where more components are being used) at the various stages of the human GI track. The products 10, 100, 200 and 300 are consumed as one entity and travel through the human GI tract, with each component releasing via the functional coating and the core matrices. This allows for targeting of each of the desired sites of bio-availability, and controlling the rate of release of the different components and their active agents.

The present invention having been thus described With particular reference to the exemplary tablets and pills, but it will be obvious that various changes and modifications may be made to these tablets and pills when preparing bespoke tablets and pills using the methods described herein.

EXAMPLES

Example 1

Preparing Customized Treatment for Diabetics with Cardiovascular Risk (Metabolic Syndrome)

In the '60s and '70s healthcare researchers began to document a clustering of elements of cardiovascular risk in certain patients that was later believed to have a unifying cause— insulin resistance. The hypothesis was given the name syndrome X. Over time the name morphed into phrase metabolic syndrome.

Key components of metabolic syndrome are central adiposity, dyslipidemia, hypertension and glucose intolerance. Chronic inflammation, pro-coagulation, and impaired fibrinolysis are also thought to play a role.

If one has one component of the syndrome, he or she is at increased risk for having one or more of the others. And the more components one has, the greater the risks to that person's health. Smoking is a factor for increased risk as well. The coexistence of these conditions in the same patient is related to an increased incidence of cardiovascular disease. Risk factors include smoking, poor diet, sedentary lifestyle and genetic predisposition. Not all patients with metabolic syndrome will have all of the component factors. Different patients will have different components, and with differing degrees of severity or progression.

Therapies are currently available to address most of the components, where risk factor control is less than optimal. Drugs for treating insulin resistance are available as exemplified by the thiazolidinediones. Statins can be used to treat dyslipidemia. And ACE inhibitors can treat hypertension. These therapies may require taking three or more different pills and strengths. How much of each drug is given a particular patient will most certainly vary from patient to patient. While it would be advantageous to create a "polypill" to assist with patient compliance with a treatment regimen. The challenge of preparing a fixed-dose polypill for every possible patient iteration is a significant one, given the possible number of combinations the original manufacturer would need to prepare and stockpile in order to address physicians' concerns about targeting drug and specific patient needs.

To illustrate, where a patient has two or more of the components of metabolic syndrome, a physician may elect to prescribe 2 or 3 drugs selected from statins, ACE inhibitors and drugs to treat insulin resistance. Specifically, the physician may elect to prescribe the statin simvastin for treating dyslipidemia in one of the 4 different currently strengths: 5 mg, 10 mg, 20 mg, 40 mg and 80 mg, an ACE inhibitor, enalapril, for treating hypertension which is sold in 4 different strengths: 2.5 mg, 5 mgm 10 mg and 20 mg and/or a thiazolidinedione, Avandia, for treating insulin resistance which is sold in 3 different strengths: 2 mg, 4 mg and 8 mg.

To manufacture all possible 2 and 3-way iterations of these strengths requires manufacturing and warehousing over 100 stock tablets to cover all iterations. However, suing the method described herein above, is one or more of the illustrated physical forms, one has only to manufacture 15 different stock preparations, 5 for simvastatin, 4 for enalapril and 3 for Avandia. Then, when the physician decides to prescribe for her patient treatment comprising 5 mg of simvastatin, 20 mg of enalapril, and 4 mg of Avandia, the producer needs only to pull these from inventory and process the three into a single final pill form. At a second visit, the physician could adjust one or more of each of the there drugs in line with the progress of the patients particular response to the multiple therapy by sending a new prescription to the manufacturer or distributor with instruction to produce the new combination from stock.

What is claimed is:

1. A method, comprising:
   a) compressing each of a plurality of formulations into a corresponding solid physical form, each of said physical forms having a concentration of active agent;
   b) stockpiling said solid physical forms with a group which has the capacity to combine a plurality of said solid physical forms into a single unit;
   c) identifying two or more of said solid physical forms to treat a particular patient;
   d) communicating said solid physical forms identified in step (c) to said group stockpiling said solid physical forms;
   e) wherein said group combines said solid physical forms identified in step (c) into said single unit; and
   f) distributing said single unit indirectly or directly to the patient.

2. A method, comprising:
   a) compressing each of a plurality of formulations into a corresponding solid physical form, each of said physical forms having a concentration of active agent;
   b) stockpiling said solid physical forms with a first group;
   c) identifying two or more of said solid physical forms to treat a particular patient;
   d) communicating said two or more physical solid forms identified in step (c) to said first group;
   e) supplying said two or more physical solid forms identified in step (c) to a second group which combines said two or more physical solid forms identified in step (c) into a single unit; and
   f) distributing said single unit indirectly or directly to the patient.

3. The method of claim 1, wherein said solid physical forms identified in step (c) are combined into said single unit with an adhesive.

4. The method of claim 2, wherein said solid physical forms identified in step (c) are combined into said single unit with an adhesive.

5. The method of claim 1, wherein said solid physical forms identified in step (c) are combined into said single unit with a weld.

6. The method of claim 2, wherein said solid physical forms identified in step (c) are combined into said single unit with a weld.

7. The method of claim 1, wherein said solid physical forms identified in step (c) are combined into said single unit with a mechanical connection.

8. The method of claim 7, wherein each of said solid physical forms has a part thereon for forming said mechanical connection with an adjacent one of said solid physical forms when combined into said single unit.

9. The method of claim 2, wherein said solid physical forms identified in step (c) are combined into said single unit with a mechanical connection.

10. The method of claim 9, wherein each of said solid physical forms has a part thereon for forming said mechanical connection with an adjacent one of said solid physical forms when combined into said single unit.

* * * * *